United States Patent
Buttle

(10) Patent No.: US 6,850,055 B2
(45) Date of Patent: Feb. 1, 2005

(54) MEASUREMENT OF THE VARIATION OF A MATERIAL PROPERTY WITH DEPTH IN A FERROMAGNETIC MATERIAL

(75) Inventor: David John Buttle, Wantage (GB)

(73) Assignee: AEA Technology plc, Didcot (GB)

(*) Notice: Subject to any disclaimer, the term of this patent is extended or adjusted under 35 U.S.C. 154(b) by 44 days.

(21) Appl. No.: 10/245,401

(22) Filed: Sep. 18, 2002

(65) Prior Publication Data

US 2003/0071614 A1 Apr. 17, 2003

(30) Foreign Application Priority Data

Oct. 17, 2001 (GB) .............................................. 0124910

(51) Int. Cl.$^7$ ............................. G01B 7/24; G01R 33/12

(52) U.S. Cl. ...................................... 324/209; 324/228

(58) Field of Search ................................ 324/209, 228, 324/232, 240

(56) References Cited

U.S. PATENT DOCUMENTS

| | | | |
|---|---|---|---|
| 3,358,225 A | 12/1967 | Peugeot | 324/40 |
| 3,742,357 A | 6/1973 | Kubo | 324/34 ST |
| 4,661,777 A | 4/1987 | Tornblom | 324/225 |
| 4,727,322 A | 2/1988 | Lonchampt | 324/229 |
| 5,394,084 A | 2/1995 | Snyder | 324/225 |
| 5,541,510 A | 7/1996 | Danielson | 324/233 |
| 5,828,211 A | 10/1998 | Scruby | 324/209 |

FOREIGN PATENT DOCUMENTS

GB          2278450          11/1994

OTHER PUBLICATIONS

Buttle et al; "Probe Modelling to Enable Biaxial Stress Measurement Depth Profiling", Studies in Applied Electromagnetics and Mechanics, 1995; vol. 8, p: 41–52 IOS Press.*

David J Buttle, William Dalzell, and Peter J Thayer; "Non–destructive Rapid Residual Stress Measurements in Rail Heads with Maps"; This paper was presented at a conference, in conference proceedings issued on Sep. 18, 2001.

D J Buttle, W Dalzell and P J Thayer; "Non–destructive Residual Stress Measurement in Rail Heads and Rolling Contact Fatigue"; INSIGHT, vol. 44, No. 6, Jun. 2002, pp 364–368.

* cited by examiner

*Primary Examiner*—N. Le
*Assistant Examiner*—Reena Aurora
(74) *Attorney, Agent, or Firm*—William H. Holt

(57) ABSTRACT

The variation in properties of a ferromagnetic material with depth below the surface is assessed in a nondestructive fashion using a probe that incorporates an electromagnet. An alternating magnetic field is generated in the electromagnet and so in the object, and a magnetic sensor is arranged to sense a magnetic field due to the electromagnet. Signals from the magnetic sensor are analysed into an in-phase component and a quadrature component, and these are mapped directly into material property and lift-off components; this analysis enables accurate measurements of material property (such as stress) to be distinguished from changes in lift-off. The measurements are repeated for at least five different frequencies of the alternating magnetic field; and the measurements at different frequencies are deconvolved assuming a functional form for the variation of material property with depth, the function having no more than five unknown constants. The stress at depths for example in the range 0.5 mm to 5.0 mm can hence be measured nondestructively.

9 Claims, 3 Drawing Sheets

MEASUREMENT OF THE VARIATION OF A MATERIAL PROPERTY WITH DEPTH IN A FERROMAGNETIC MATERIAL

This invention relates to a method and apparatus for measuring material properties within a ferromagnetic material, using an electromagnetic probe, for example for measuring stress.

The stresses in structures such as rails, bridges and pipelines, complex mechanisms such as vehicles and machinery, or simple devices such as struts, cables or bearings arise from various causes including changes of temperature, and the loads and pressures due to use. There may also be residual stresses arising from the fabrication of the structure or device, and any bending that the structure or device was subjected to during construction; the residual stresses arising from fabrication will also be affected by any stress-relieving heat treatment. In some situations (such as pipelines) the principal stress directions can be expected to be in particular directions (circumferential and longitudinal), whereas in other situations the stress directions are also unknown. A variety of magnetic techniques are known to have some sensitivity to stress, although magnetic measurements are usually also affected by other material properties such as microstructure. A way of measuring stress in a steel plate is described in U.S. Pat. No. 5,828,211 (GB 2 278 450), this method using a probe containing an electromagnetic core to generate an alternating magnetic field in the plate, and then combining measurements from two sensors, one being a measure of stress-induced magnetic anisotropy (SMA), and the other being a measure of directional effective permeability (DEP). The probe is gradually turned around so the magnetic field has a plurality of different orientations in the plate, and these measurements are taken at each such orientation. The probe enables the stress to be measured near the surface, the depth of penetration depending upon the frequency.

According to the present invention there is provided a method for measuring how a material property that affects permeability in an object of ferromagnetic material varies with depth below the surface, the method using at least one probe, the or each probe comprising an electromagnet means, means to generate an alternating magnetic field in the electromagnet means and consequently in the object, and a magnetic sensor arranged to sense a magnetic field due to the electromagnet means; and the method comprising resolving signals from the magnetic sensor into an in-phase component and a quadrature component; mapping the in-phase and quadrature components directly into material property and lift-off components; and deducing a material property from the material property component so determined; repeating these measurements for at least five different frequencies of the alternating magnetic field; and deconvolving the measurements of material property obtained at different frequencies by assuming a functional form for the variation of material property with depth, the function having no more unknown constants than the number of different frequencies, assuming values for the unknown constants, assessing the accuracy of the values of the unknown constants in the function by comparing the observed measurements to the corresponding predicted measurements with those values of the unknown constants, and adjusting the values of the unknown constants to obtain the best fit between observed measurements and predicted measurements, so as to determine how the material property varies with depth.

Surprisingly it has been found that, by compensating for any changes in lift-off in this manner so as to ensure accurate measurements of material property, and by assuming a functional form for the variation, a convergent and consistent deconvolution can be performed. Accuracy in the measurements and their interpretation is absolutely fundamental, because even at low frequencies (when greater penetration is expected) the bulk of the response is due to the material nearer to the surface.

Furthermore, at lower frequencies the signal strength decreases (if the sensor is a coil), and the stress sensitivity also decreases. It must also be understood that the penetration depth cannot be assessed accurately by a "skin depth" calculation, because if the stress is varying with depth there must be a consequential change in magnetic properties with depth. The invention enables the measurement in situ of the stress variation with depth, for depths up to about 8 mm.

The mapping requires a preliminary calibration, with a specimen of the material, to determine how the in-phase and quadrature components of the signal vary with lift-off (at a constant stress) and vary with stress (at a constant lift-off), and deducing from the calibration measurements the applicable mapping for any stress and any lift-off. The mapping may be represented in the impedance plane (i.e. on a graph of quadrature component against in-phase component) as two sets of contours representing signal variation with lift-off (for different values of stress) and signal variation with stress (for different values of lift-off), the contours of both sets being curved. The contours of one set intersect the contours of the other set at non-orthogonal angles. In a preferred method of mapping the angles at which the contours of one set intersect the contours of the other set along any one line of constant stress are all the same. Hence measurements taken along one contour of each set enable the positions of the other contours of each set to be determined.

Surprisingly this simple mapping has been found to give an accurate representation of the variation of the signals with material property (e.g. stress), and provides a simple way to distinguish these variations from variations arising from lift-off or other geometrical variations such as surface texture or curvature.

Preferably the electromagnet means comprises an electromagnetic core and two spaced apart electromagnetic poles, and the magnetic sensor is preferably arranged to sense the reluctance of that part of the magnetic circuit between the poles of the electromagnet means. It is also desirable to arrange for such measurements to be taken with a plurality of different orientations of the magnetic field, at a single location on the object. This may be achieved using a single probe that is rotated at that location, measurements being taken with different orientations of the probe, or using an array of probes of different orientations that are successively moved to that location. In either case, the sensor or sensors provide a measure of the permeability of the material through which the flux passes between the poles, and so provide a signal indicative of the effective permeability of the material; the corresponding measurements at different probe orientations at a location on the object hence indicate the effective permeability in different directions, which is referred to as directional effective permeability (DEP).

The probe, or at least some of the probes, may also include a second magnetic sensor between the two poles and arranged to sense magnetic flux density perpendicular to the direction of the free space magnetic field between the poles. This second sensor would detect no signal if the material were exactly isotropic; however stress induces anisotropy into the magnetic properties of the material, and so the signals received by the second sensor are a measure of this stress-induced magnetic anisotropy (SMA). The variations in the SMA signals at different probe orientations, at a location on the object, enable the directions of the principal stress axes to be accurately determined. The SMA signals can also be related to the stress; but cannot be corrected for lift-off in the way described above.

The DEP signal from the or each probe is preferably backed-off, i.e. processed by first subtracting a signal equal to the signal from that sensor with the probe adjacent to a stress-free location. The backed-off signal is then amplified so the small changes in DEP due to stress are easier to detect. This backing off is performed after resolving into in-phase and quadrature components but before performing the mapping. Preferably the DEP signals from the or each probe are digitized initially, and the backing-off and resolution are performed by analysis of the digital signals.

Preferably the number of frequencies at which measurements are made is at least ten, and preferably even more for example 30 or 40 different frequencies. The number of unknown constants is preferably no more than half the number of different frequencies. The frequencies should be selected to ensure that observations can be made over the entire range of depths at which variation in stress is expected. Consequently it may be desirable to cover a very wide range of frequency, for example from 150 kHz (for a penetration of only about 15 μm in mild steel), down to say 5 Hz (which in mild steel provides penetration of about 5 mm).

Generally, the more different probe orientations are used for taking measurements the more accurate the determination of stress levels and principal axes can be. In many cases the principal stress axes can be assumed to be aligned in particular directions—axial and circumferential directions in the case of a pipe, for example—so that the signal maxima for DEP would be expected to be along these directions, and the signal maximum for SMA would be along the bisection angles between these directions.

The invention will now be further and more particularly described, by way of example only, and with reference to the accompanying drawings, in which.

Figure 1:
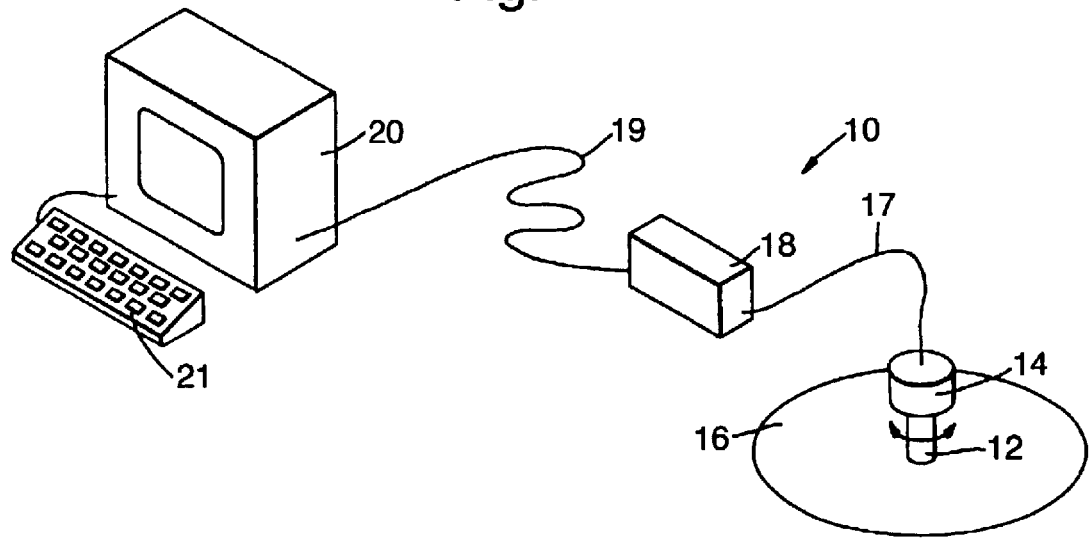
FIG. 1 shows a diagrammatic view of an apparatus for measuring stress.

Referring to FIG. 1, a stress measuring apparatus 10 includes a sensor probe 12 comprising sensors for both DEP (directional effective permeability) and SMA (stress-induced magnetic anisotropy), the probe 12 being attached to an electric motor 14 which can be held by an operator, so the motor 14 can turn the probe 12 with one end adjacent to a surface of a steel object 16 in which the stress is to be determined. The sensor probe 12 and motor 14 are connected by a 2 m long umbilical cable 17 to a signal conditioning/probe driver unit 18. The unit 18 is connected by a long umbilical cable 19 (which may for example be up to 300 m long) to an interface unit within a microcomputer 20, which has a keyboard 21. Operation of the apparatus 10 is controlled by software in the microcomputer 20.

The interface unit within the microcomputer 20 generates sine and cosine functions at an angular frequency selectable by software, and buffers the sine waveform for transmission to the unit 18 for driving the probe 12. The amplitude of the transmitted waveform is also selectable by software. It also provides signals to control the motor 14 and hence the angular position of the probe 12. The interface unit also provides control signals to the unit 18 to select which of the signals available from the probe 12 is to be transmitted for analysis. It demodulates the selected input signal (DEP or SMA) to derive its in-phase and quadrature components, filters the demodulated signal to remove high frequency components and to reduce noise, and converts the analogue signals to digital form for input to the computer 20. It also detects the angular position of the probe 12 from signals provided by a position encoder (not shown) on the motor 14.

The long umbilical cable 19 incorporates a coaxial cable to transmit the selected signal (DEP or SMA), and wires to control which signal is selected, to control the motor 14, to transmit signals from the position encoder, to transmit the sinusoidal waveform, and to convey electrical power. The unit 18 converts the drive waveform from a voltage to a current drive for the probe 12; buffers and amplifies the DEP and SMA signals from the probe 12; and selects which signal is to be transmitted to the microcomputer 20. It also buffers the signals from the position encoder for transmission, and drives the motor 14 in response to control signals.

Figure 2:
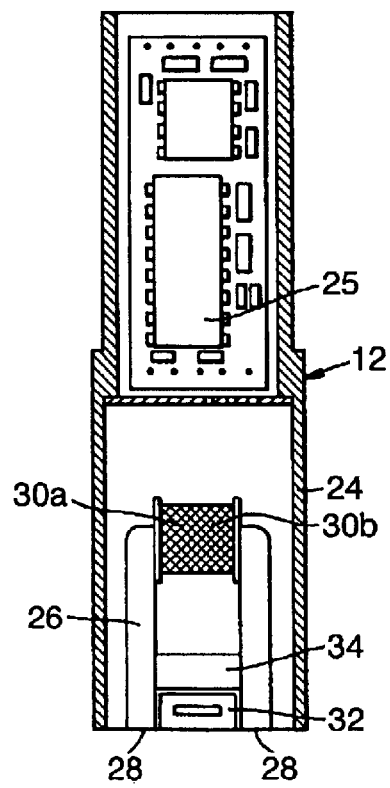
FIG. 2 shows a longitudinal sectional view of a probe for use in the apparatus of FIG. 1.

Referring now to FIG. 2, the probe 12 is shown detached from the motor 14, in longitudinal section although with the internal components shown in elevation (the connecting wires within the probe 12 are not shown). The probe 12 comprises a cylindrical brass casing 24 of external diameter 16.5 mm and of overall height 60 mm, the upper half being of reduced diameter whereby the probe 12 is attached to the motor 14. The upper half of the casing 24 encloses a head amplifier 25. The lower half encloses a U-core 26 of laminated mu-metal (a high permeability nickel/iron/copper alloy) whose poles 28 are separated by a gap 7.5 mm wide, and are each of width 2.5 mm, and of thickness 10 mm (out of the plane of the figure). The poles 28 are in the plane of the lower end of the casing 24, which is open. Around the upper end of the U-core 26 is a former on which are wound two superimposed coils 30a and 30b. One coil 30a (which has 200 turns) is supplied with the sinusoidal drive current from the unit 18; the other coil 30b (which has 70 turns) provides DEP signals. Between the two poles 28 is a former on which is wound a 1670-turn rectangular coil 32, about 4 mm high and 6 mm wide, and 6 mm-square as seen from below, the windings lying parallel to the plane of the figure so the longitudinal axis of the coil 32 is perpendicular to the line between the centres of the poles 28. The coil 32 is supported by a support plate 34 fixed between the arms of the U-core 26 so the lower face of the coil 32 is in the plane of the poles 28. The coil 32 provides the SMA signals. Both the DEP and the SMA signals are amplified by the head amplifier 25 before transmission to the unit 18.

In operation of the system 10, the motor 14 is supported so the lower end of the probe 12 is adjacent to the surface of the object 16 and the longitudinal axis of the probe 12 is normal to the surface. An alternating current of the desired frequency and amplitude is supplied to the drive coil 30a, so the magnetic field in the object 16 oscillates about zero with an amplitude much less than saturation. The probe 12 is first placed adjacent to a region of the object 12 where the stresses are negligible. The in-phase and quadrature components of the DEP signal (i.e. the component in phase with the drive current, and the component at 90° to the drive current) received by the microcomputer 20 are each backed off to zero, and the backing off values are then fixed. During all subsequent measurements the DEP components are backed off by these same amounts (i.e. subtracting a signal equal to the component observed when in a stress-free location).

Measurements can be taken by placing the probe 12 adjacent to a region in which material properties such as stress are to be measured. The orientation of the line joining the centres of the poles 28 (referred to as the orientation of the probe 12) is noted relative to a fixed direction on the surface. The motor 14 is then energized to rotate the probe 12, for example in a step-wise fashion 10° at a time through a total angle of 360°. At each orientation of the probe 12 the quadrature SMA signal is measured, and the DEP components are measured (and backed off). These measurements are made at several different frequencies, as discussed below, and at every frequency measurements are made of DEP. At least with flat or uniformly curved surfaces, measurements of SMA may also be made.

It will be appreciated that the procedure of the invention is applicable with many different probes. The probe 12 might for example be modified by using a U-core 26 of a different material such as silicon iron (which can provide higher magnetic fields), or indeed the drive coil might be air-cored. The probe might be of a different shape or size, for example for inspecting surface stress in a small bearing it may be appropriate to use a probe of diameter as small as 3 mm, while for inspecting a large steel pipe it may be appropriate to use a probe of diameter say 75 mm.

The SMA signals with a flat surface vary sinusoidally with probe orientation, so the orientation at which they have their maxima and minima can be determined. The directions midway between these two orientations are the directions of the principal stress axes. Measurements of SMA are therefore useful if the principal stress directions are unknown. The values of DEP also vary sinusoidally with probe orientation, and the values are observed at the principal stress directions. If the principal stress directions are already known, then the probe 12 might instead be merely oriented to those directions, and DEP measurements made; no rotation of the probe 12 would be necessary.

Figure 3:
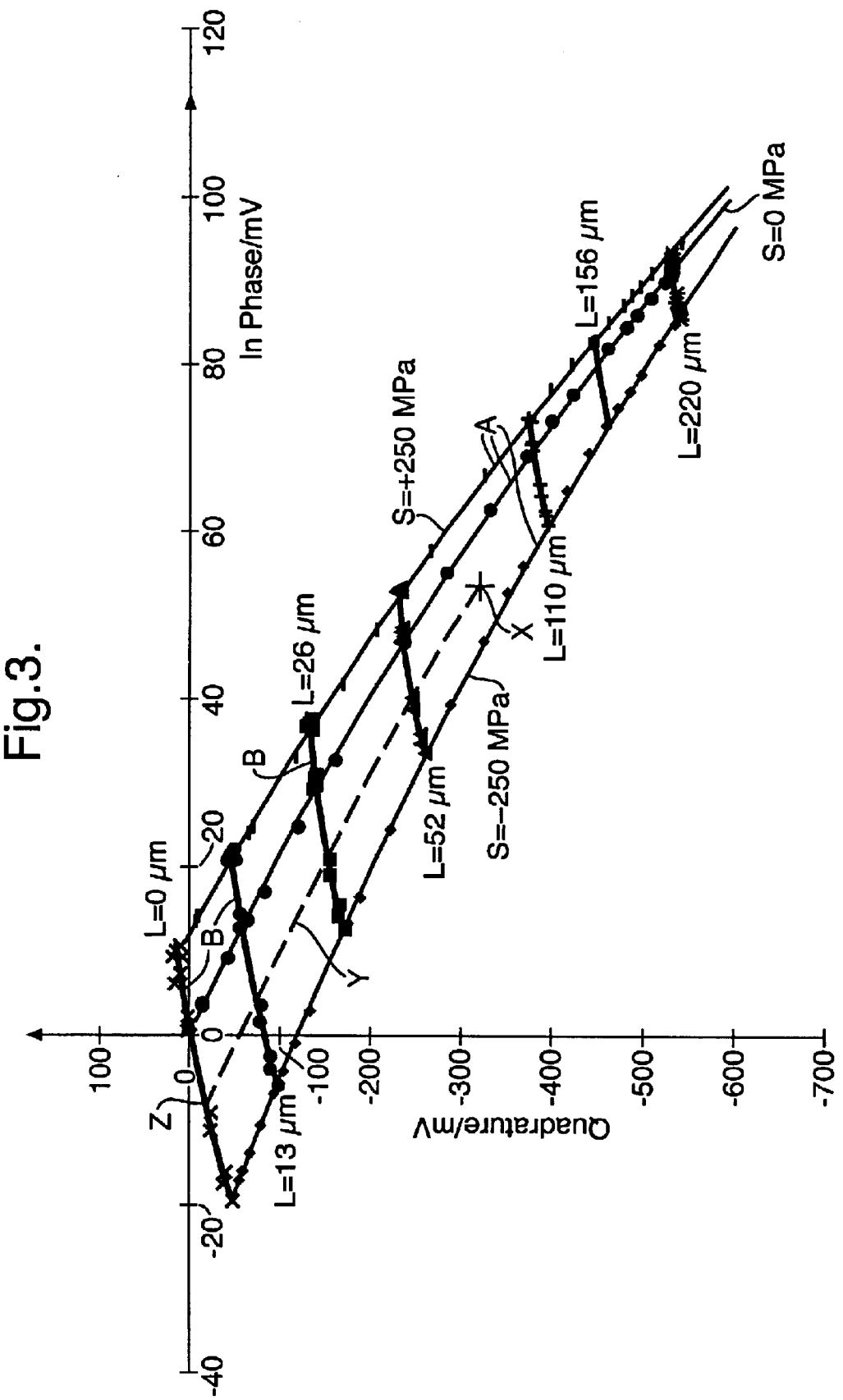
FIG. 3 shows graphically the variation of the backed-off quadrature and in-phase components of DEP with variations of lift-off, and with variations of stress.

The values of the stresses in the directions of the principal stress axes can be determined from the experimental measurements of DEP with the probe 12 oriented in those directions. This requires calibration of the apparatus 10, taking measurements on a sample of material of the same type as that of the object 16, while subjecting it to a variety of different stresses. This may be done with a rectangular strip sample in a test rig, DEP measurements being made at the centre of the sample where the principal stress direction is aligned with the axis of the test rig. Referring to FIG. 3 this shows the backed-off DEP in-phase and quadrature components obtained in such a test rig, the measurements being made with a drive frequency of 70 Hz, and the specimen being a steel bar. A first set of measurements were made at progressively larger values of lift-off, L, but with no stress, S. This gives the lift-off contour A, the lift-off varying between 0 and 220 $\mu$m. Similar lift-off contours A are obtained for other fixed values of stress, those for S=250 MPa tension and compression being shown. Measurements were then made at a range of different fixed values of lift-off, L, with varying stresses, S (both compression and tension), providing the contours B.

It will be appreciated that the contours A are curved, and the contours B are not orthogonal to the contours A, but that they intersect at substantially constant angles at least along any line A of constant stress. Consequently it is only necessary to make calibration measurements sufficient to plot a few such contours A and B, and the shapes of the other contours can be predicted. It has also been found that this intersection angle, and the curvature of the contours, are characteristic of the material.

After calibrating the probe 12 in this manner, measurements of stress can be readily made from observations of DEP signals (resolved and backed off), as the contours enable the changes due to lift-off to be readily distinguished from changes due to stress. Any particular position in the impedance plane (i.e. in the graph of quadrature against in-phase components) corresponds to a particular value of stress and a particular value of lift-off. The mapping between (in-phase, quadrature) coordinates and (stress, lift-off) coordinates may be carried out graphically, referring to such contours, or by calculation. For example if the DEP signal has the in-phase and quadrature components of the position marked X, this corresponds to a lift-off of about 80 $\mu$m and a stress of about 125 MPa. Alternatively this value X may be translated (along the broken line Y) along a contour A of constant stress to find the in-phase and quadrature components at position Z that would be obtained with zero lift-off.

The value of stress found in this way is, it will be appreciated, the uniaxial stress that would provide that value of the DEP signal. If the stresses are actually biaxial, then a further calibration must be carried out with a cross-shaped sample in a test rig, DEP measurements being made at the centre of the sample where the principal stress directions are aligned with the axes of the test rig. Hence a graph or map may be obtained for a range of values of stress on one axis (say the x-axis) and for a range of values of stress in the other axis (say the y-axis), with contours each of which shows the values of biaxial stress that give a particular value of apparent uniaxial stress along the x-axis; and a similar graph may be obtained with contours showing values of biaxial stress that give a particular value of apparent uniaxial stress along the y-axis. Hence from measurements of apparent uniaxial stress along the two principal stress axes obtained as described earlier, the biaxial stress can be determined.

It will again be appreciated that the biaxial stress may be determined either graphically or by calculation in this way. Apparent values of uniaxial stress (in MPa) may be used for this purpose, or alternatively the numerical value of DEP (in mV), either the in-phase or quadrature value, obtained by eliminating the effect of lift-off as described in relation to FIG. 3, may be used.

The electromagnetic field created by the probe 12 will induce eddy currents within the object 16, and (if we can assume that the width of the probe 12 is considerably greater than the penetration depth) the flux density B will therefore decay exponentially with depth, z, according to the equation:

$$B=B_0 \exp(-z/\delta) \text{ where } \delta=1/(\pi\mu_0\mu_r fk)^{1/2}$$

where $\mu_0$ is the permeability of free space, $\mu_r$ is the low field relative permeability of the ferromagnetic material, k is its electrical conductivity, and f is the frequency. The parameter $\delta$ may be referred to as the skin depth. Furthermore the amplitude of the induced voltage, V, in the sensor coil (e.g. the DEP coil 30b) of n turns can be expressed (ignoring eddy current or hysteresis effects) as:

$$V=2\pi f n NI/\text{magnetic reluctance}$$

where the drive coil 30a has N turns and carries a sinusoidal current of amplitude I. The magnetic reluctance is that of the entire magnetic circuit, including the core 26, the air gap between the core and the object, and the magnetic path through the surface layers of the object 16. One would therefore expect that the reluctance R could be expressed as:

$$R=\text{the sum of three terms of the form}:L/(\mu_0\mu_r wt)$$

where L is the length of the magnetic path through the material, w its width, and t its thickness. However, a complication arises from the fact that the magnetic properties represented by the relative permeability, $\mu_r$, within the object 16 are themselves a property of the stress, and so must be assumed to vary with depth z. In the equation for $\delta$ we must replace $\mu_r$ by $\mu(z)$, so that $\delta$ is itself a function of z. Consequently a more accurate representation of the variation of flux density is:

$$B(z)=B_0\exp(-\int dz/\delta(z))$$

Consequently the voltage equation can be written as:

$$V = 2\pi\mu_0 f n N I \Big/ \left\{(L_{core}/\mu_{core}\text{wt}) + (L_{air}/\text{wt}) + (L\pi\mu_0 fk/w)\int \exp\!\left(-\int dz/\delta(z)\right)\!dz\right\}$$

where the value of w may be somewhat larger in the object 16 (the third term) than in the core 26.

The function $\delta(z)$ in principle contains within it the depth variation of the magnetic property, and therefore, via calibration, the variation of stress. If deconvolution is carried out explicitly so as to obtain the function $\delta(z)$ it has been found that the solution does not converge, because small errors in measurements produce large swings in the predicted variation of stress with depth, that is to say many totally different depth profiles can lead to the same (integrated) measurements at the surface. It is therefore necessary to assume a functional form for $\delta(z)$ or equivalently for $\mu(z)$. This approach has proved to be effective, but limits the stress profiles that can be measured to the chosen functional form. The degree to which the function fits the data can be assessed by an RMS error, so it is possible to try using different functions until a good fit is found. The ultimate result is a smooth variation through the stress depth profile.

A functional form that has been found suitable in many cases is:

$$\mu(z)=(a+bz)\exp(-cz)+(d+ez)$$

that is to say a linear function combined with an exponential function with a linear coefficient, in which the unknown coefficients a . . . e must be found from the experimental measurements taken at the surface.

For implementation there are two further issues. The voltage equation above indicates that the voltage signals increase rapidly with frequency. Secondly, the instrumentation may itself have a response that varies with frequency. To compensate for these variations it is necessary to normalise the data against the measured frequency response M(f). The measured response can be determined in two ways: either by making a measurement at zero stress, and at a non-zero uniform stress, S:

$$M_1(f)=M_s(f)-M_0(f)$$

or alternatively by making a measurement with the probe 12 held first in air, and then on the surface of the steel object 16:

$$M_2(f)=M_{steel}(f)-M_{air}(f)$$

The first method has the advantage of yielding the true frequency response, but requires an unstressed sample; the second approach is only approximate, as the steel object 16 may be under stress, but since $M_2 \gg M_1$ the error is typically only a few percent.

To determine the best fit for the magnetic permeability depth profile, $\mu(z)$, to a set of measurements m(f) made at a single position on the surface at p different frequencies, the root mean square is calculated for the p different values of the error:

$$\text{error}=[m(f)\{M(F)/M(f)\}-V_{f}\mu(z)(f)\{V_0(F)/V_0(f)\}]$$

where $V_{82}(z)$ is the value of V calculated by the equation given above assuming a particular function for $\mu(z)$, while $V_0$ is the corresponding value calculated assuming zero stress (and therefore a constant value of $\mu_r$), and where f is the frequency at which a measurement is made, and F is a reference frequency such as 70 Hz. Thus the normalisation factors are themselves normalised with respect to values at this reference frequency. This enables the coefficients to be optimised for a particular functional form for $\mu(z)$. The procedure can be repeated for different functional forms, if desired, and the best one, i.e. the one providing the smallest RMS error, can then be selected as being the most realistic. It is thus possible to ascertain the variation of magnetic permeability with depth.

To determine the variation of stress with depth, the value of $\mu(z)$ is determined for several different depths q. For each such value a corresponding value of V can be calculated, using the equation above, taking the magnetic permeability as having the constant value $\mu(q)$ at all depths. This may be related to stress using the calibration technique discussed earlier in relation to FIG. 3. (It will be appreciated that the above procedure will require the functional variation of magnetic permeability with depth to be determined for each of the principal stress axes separately, and to then be combined in order to determine the stress.)

To obtain accurate profiles the number of different frequencies at which measurements are taken must clearly be at least as many as the number of coefficients in the function assumed for the variation. It has been found preferable to have at least twice as many different frequencies as the number of coefficients. Furthermore the frequencies must be selected so as to cover the depth range under investigation. The minimum depth at which the stress can be determined can be related to the highest frequency at which measurements were taken, this minimum depth being about a quarter of the skin depth, $\delta$, at that frequency. Similarly, the maximum depth at which the stress can be determined is related to the lowest frequency at which measurements were made, and is about 1.5 times the skin depth, $\delta$, at that frequency. The different frequencies are preferably selected so that they correspond to equal increments of the skin depth, $\delta$. Alternatively, it may be desired to have more measurements nearer to the surface, and the frequencies would be selected accordingly.

Figure 4A:
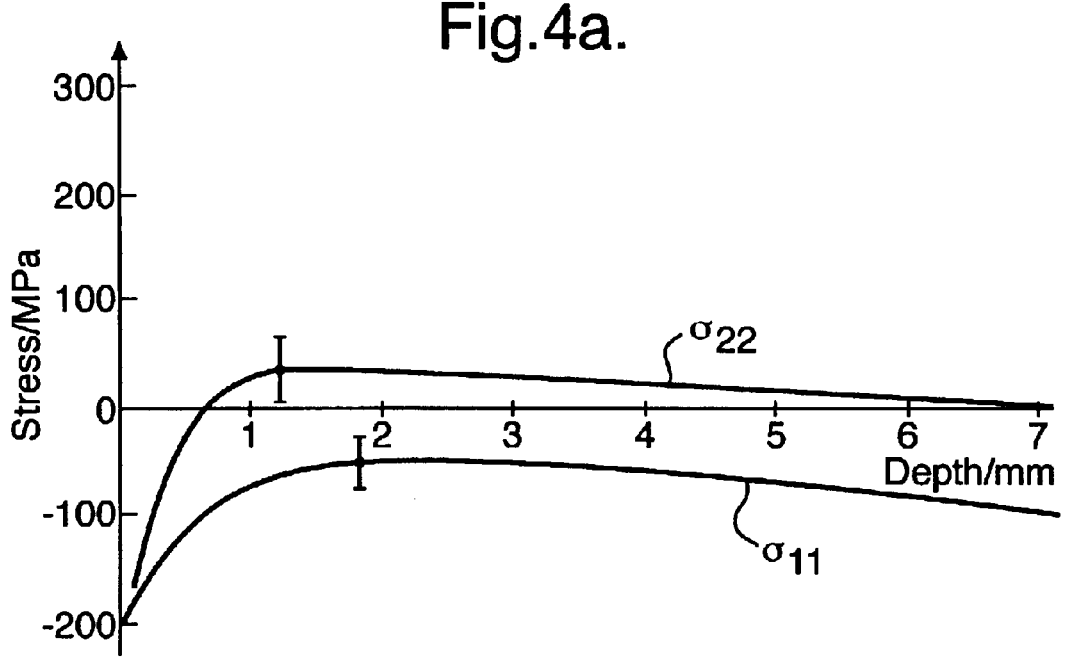
FIGS. 4a and 4b show graphically the variation of stress with depth below the surface in two different objects.
Figure 4B:
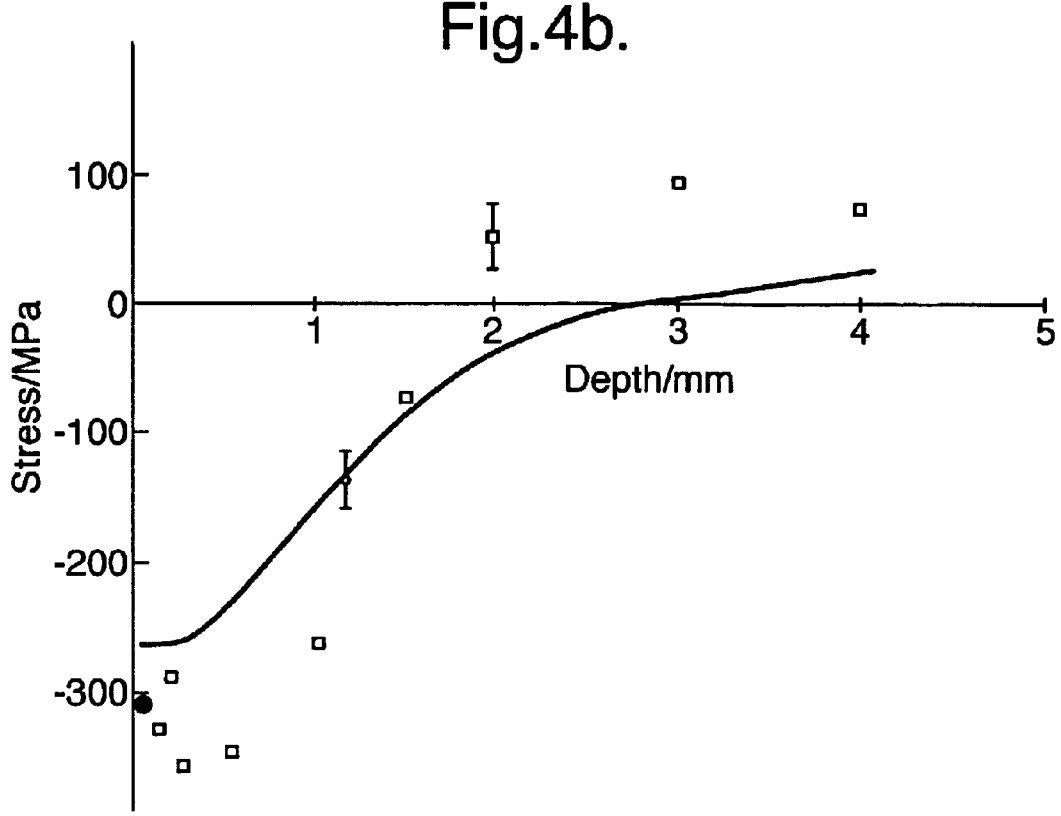

Referring now to FIGS. 4a and 4b, these show graphically the variation of stress with depth in two different objects, in each case the smooth curve showing the variation of stress with depth as determined by the method described above. Referring firstly to FIG. 4a, this shows values of stress in a section of railway rail that had been in use for 15 years, showing the stresses below the surface of the railhead. The stresses are significantly different in the two principal axes; one principal axis is close to the longitudinal axis of the rail (graph marked $\sigma_{11}$), and the other principal axis is approximately transverse (graph marked $\rho_{22}$). In each case one point has been marked on the graph, along with an error bar to indicate the uncertainty. As far as the generally longitudinal stress $\sigma_{11}$ is concerned, this is compressive at all depths, being maximum near the surface. In contrast, the generally transverse stress $\sigma_{22}$ is compressive near the surface, the stress decreasing in magnitude to zero at a depth of about 0.7 mm, and then being tensile at greater depths.

Referring now to FIG. 4b, this shows the variation of stress with depth below the surface of a specimen of spring steel that had been subjected to laser shock peening. The continuous line shows the variation of stress as measured by the method described above, the stress near the surface being compressive and about 270 MPa, and below the surface the magnitude of the stress gradually decreases to zero at about 2.8 mm, and then being tensile. These measurements may be compared to those obtained by other stress measuring techniques. The black circle indicates a stress measurement obtained by an X-ray diffraction technique. This can measure the stress in a surface layer of thickness about 5 $\mu$m. This indicates a compressive stress near the surface of about 310 MPa. The hollow squares show measurements of stress at different depths below the surface measured by a neutron diffraction technique, suggesting a compressive stress near the surface of about 300 MPa, decreasing to zero at about 1.8 mm and being tensile at greater depths (at least up to about 4 mm). An error bar is shown on one of the hollow squares, to indicate the uncertainty of these measurements. Although the neutron diffraction measurements do not give an identical stress distribution to that given by the method of the present invention, nevertheless the overall pattern of the stress variation is very similar.

I claim:

1. A method for measuring how a material property that affects permeability in an object of ferromagnetic material varies with depth below the surface, the method using at least one probe, the or each probe comprising an electromagnet means, means to generate an alternating magnetic field in the electromagnet means and consequently in the object, and a magnetic sensor arranged to sense a magnetic field due to the electromagnet means; and the method comprising resolving signals from the magnetic sensor into an in-phase component and a quadrature component; mapping the in-phase and quadrature components directly into material property and lift-off components; and deducing a material property from the material property component so determined; repeating these measurements for at least five different frequencies of the alternating magnetic field; and deconvolving the measurements of material property obtained at different frequencies by assuming a functional form for the variation of material property with depth, the function having no more unknown constants than the number of different frequencies, assuming values for the unknown constants, assessing the accuracy of the values of the unknown constants in the function by comparing the observed measurements to the corresponding predicted measurements with those values of the unknown constants, and adjusting the values of the unknown constants to obtain the best fit between observed measurements and predicted measurements, so as to determine how the material property varies with depth.

2. A method as claimed in claim 1 wherein the mapping is represented in the impedance plane (i.e. on a graph of quadrature component against in-phase component) as two sets of contours representing signal variation with lift-off (for different values of stress) and signal variation with stress (for different values of lift-off), the contours of both sets being curved.

3. A method as claimed in claim 1 wherein the electromagnet means comprises an electromagnetic core and two spaced apart electromagnetic poles, and the magnetic sensor is arranged to sense the reluctance of that part of the magnetic circuit between the poles of the electromagnet means.

4. A method as claimed in claim 1 wherein the number of frequencies at which measurements are made is at least ten.

5. A method as claimed in claim 1 wherein the frequencies are selected to ensure that observations are made over the entire range of depths at which variation in stress is expected.

6. A method as claimed in claim 1 wherein the function is of the form: $\mu(z)=(a+bz)\exp(-cz)+(d+ez)$, where z is the depth.

7. A method as claimed in claim 1 wherein the accuracy of the values of the unknown constants in the function is assessed by calculating a root mean square error from the errors given by the differences between the observed measurements and the corresponding predicted measurements with a particular set of values of the constants.

8. A method as claimed in claim 7 wherein, in calculating the error, both the observed measurement and the predicted measurement are normalised to a value at a preset frequency.

9. A method as claimed in claim 8 wherein the preset frequency is a frequency at which calibration measurements have been made to determine the mapping.

* * * * *